(12) United States Patent
Costabile

(10) Patent No.: US 7,862,613 B1
(45) Date of Patent: Jan. 4, 2011

(54) DEVICE AND METHOD FOR ATTACHING HAIR

(76) Inventor: James Costabile, 136 Stonehenge Ter., Clark, NJ (US) 07066

( * ) Notice: Subject to any disclaimer, the term of this patent is extended or adjusted under 35 U.S.C. 154(b) by 0 days.

(21) Appl. No.: 12/755,511

(22) Filed: Apr. 7, 2010

(51) Int. Cl.
A61F 2/10 (2006.01)

(52) U.S. Cl. .................... 623/15.11; 132/201

(58) Field of Classification Search ... 623/15.11–15.12; 132/201; 606/187
See application file for complete search history.

(56) References Cited

U.S. PATENT DOCUMENTS

| | | | |
|---|---|---|---|
| 1,378,147 A | 5/1921 | Tapscott | |
| 1,490,479 A | 4/1924 | Noel | |
| 3,643,658 A | 2/1972 | Steinemenan | |
| 3,662,766 A | 5/1972 | Maassen et al. | |
| 3,694,819 A | 10/1972 | Meyer | |
| 3,858,247 A | 1/1975 | Bauman | |
| 3,862,453 A | 1/1975 | Widdifield | |
| 3,877,570 A | 4/1975 | Barry | |
| 4,037,274 A | 7/1977 | Agosta | |
| 4,050,100 A | 9/1977 | Barry | |
| 4,144,876 A | 3/1979 | DeLeo | |
| 4,265,246 A | 5/1981 | Barry | |
| 4,753,656 A | 6/1988 | Tofield et al. | |
| 4,870,957 A | 10/1989 | Goble et al. | |
| 4,969,903 A | 11/1990 | Valle | |
| 5,370,662 A | 12/1994 | Stone et al. | |
| 5,697,979 A | 12/1997 | Pignataro | |
| 5,741,336 A * | 4/1998 | Fraser | 623/15.11 |
| 6,561,197 B2 * | 5/2003 | Harrison | 132/201 |
| 2002/0179108 A1 * | 12/2002 | Harrison | 132/201 |
| 2007/0106394 A1 * | 5/2007 | Chen | 623/23.76 |
| 2009/0199861 A1 * | 8/2009 | Paris | 132/201 |
| 2010/0037908 A1 * | 2/2010 | Hatcher et al. | 132/201 |

* cited by examiner

Primary Examiner—Suzette J Gherbi
(74) Attorney, Agent, or Firm—Arthur Jacob

(57) ABSTRACT

A fitting and a method for utilizing one or more of such fittings are described for securing supplemental hair to a person's head, along the outer surface of the person's scalp, to create an enhanced, natural appearance independent of the population and location of any natural hair on the person's head. Each fitting includes a base and a longitudinal bridge rising from the base to establish an eye providing a lateral path beneath the bridge. Each base is embedded beneath the outer surface of the person's scalp to secure the corresponding fitting at a selected strategic location on the person's head with the bridge projecting from the outer surface to provide a corresponding attachment site. Supplemental hair is juxtaposed with and secured to each bridge with a corresponding ligature passed through the eye of each corresponding bridge.

12 Claims, 4 Drawing Sheets

DEVICE AND METHOD FOR ATTACHING HAIR

The present invention relates generally to the attachment of hair to the human head and pertains, more specifically, to a device and method for securing hair to a human head, usually as a supplement to a person's natural hair, so as to provide an enhanced, natural appearance which will last over an extended service life.

A well-received method currently in use for supplementing a person's natural hair to provide an enhanced, natural appearance consists of securing supplemental hair to existing natural hair, with care being taken to assure that melding of the supplemental hair with the natural hair is accomplished so skillfully as to go undetected by ordinary observation. While highly effective, the method suffers a drawback in that with the passage of time, the natural hair will grow out, taking with it the attached supplemental hair and adversely affecting the desired natural look. In addition, the attachment locations may become exposed to view, with the concomitant defeat of the natural look sought by the person. In order to overcome these drawbacks, adjustments are made from time to time to restore the natural appearance. Further, this current method, while highly desirable and widely pursued, requires that enough natural hair be available to provide a suitable number of strategically located sites for the attachment of supplemental hair to attain the desired, natural appearance.

The present invention accomplishes the securement of supplemental hair to a persons's head, while avoiding the above-described drawbacks. As such, the present invention attains several objects and advantages, some of which are summarized as follows: Provides a human head with one or more attachment sites for securing hair at strategic locations to supplement natural hair present on the head and attain an enhanced appearance independent of the population and location of natural hair present on the head; facilitates the attachment of supplemental hair to a human head at one or more locations selected for best attaining a natural aesthetic appearance; enables the establishment of strategically located hair attachment sites, utilizing simple, minimally invasive procedures; establishes an aesthetically pleasing appearance capable of long-term service without requiring periodic adjustments to maintain the pleasing appearance; permits the conduct of regular hair care without the necessity for extraordinary procedures to compensate for the presence of secured supplemental hair; simplifies the attainment of a secure and reliable attachment of supplemental hair to a person's head; encourages widespread adoption of the attachment of supplemental hair to enhance appearance; provides for a reliable attachment of supplemental hair for exemplary long-term performance.

The above objects and advantages, as well as further objects and advantages, are attained by the present invention, which may be described briefly as a fitting for placement at a selected location on a person's head, embedded beneath the outer surface of the person's scalp to secure the fitting at the selected location, to enable securement of hair to the person's head, the fitting comprising: a base extending in longitudinal and lateral directions for placement between the outer surface of the scalp and the underlying bone of the person's skull, spaced from both the outer surface and the bone, the base having an obverse surface and a reverse surface; and a bridge integral with the base, the bridge extending in longitudinal directions between opposite ends and being raised from the base intermediate the opposite ends in an latitudinal direction to establish an eye between the bridge and the obverse surface of the base, the eye providing an open path extending in lateral directions, the bridge having a continuous, smooth contoured upper surface configuration extending from end to end of the opposite ends and spaced latitudinally from the obverse surface to pass over the eye, such that upon embedding the base beneath the outer surface of the scalp, the contoured configuration of the bridge will project latitudinally from the scalp unobtrusively, while exposing the eye for reception of a ligature which will secure hair to the fitting.

In addition, the present invention provides a method for securing supplemental hair to a person's head, along the outer surface of the person's scalp, to create an enhanced natural appearance independent of any natural hair on the person's head, the method comprising: selecting at least one strategic location on the person's head; placing at least one fitting at the selected location, the fitting including a base having an obverse surface and a reverse surface, and a bridge, the base extending in longitudinal and lateral directions, and the bridge extending in the longitudinal directions and rising from the base in an latitudinal direction to establish an eye between the bridge and the obverse surface of the base, the eye providing an open path extending in lateral directions; embedding the base beneath the outer surface of the person's scalp with the base placed between the outer surface of the scalp and the underlying bone of the person's skull, spaced from both the outer surface and the bone, to secure the fitting at the selected strategic location with the bridge projecting latitudinally from the scalp to expose the eye for reception of a ligature; juxtaposing supplemental hair with the bridge; passing a ligature along the open path through the eye; and securing the juxtaposed supplemental hair to the bridge with the ligature.

The present invention will be understood more fully, while still further objects and advantages will become apparent, in the following detailed description of preferred embodiments of the invention illustrated in the accompanying drawing, in which.

Figure 1:
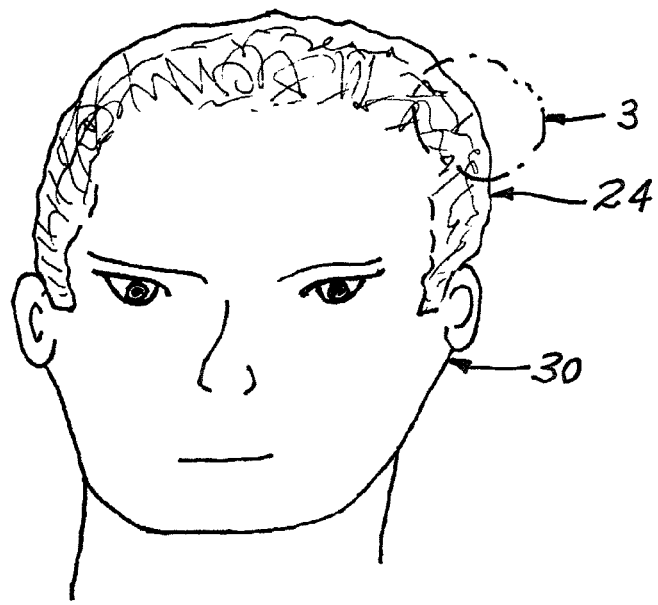
FIG. 1 is a pictorial illustration showing a person who has been subjected to a currently-practiced procedure.
Figure 2:
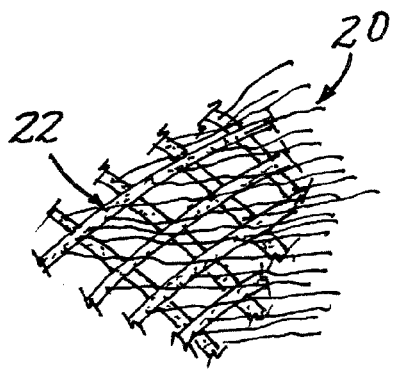
FIG. 2 is a fragmentary pictorial illustration of a form in which supplemental hair is made available currently.
Figure 3:
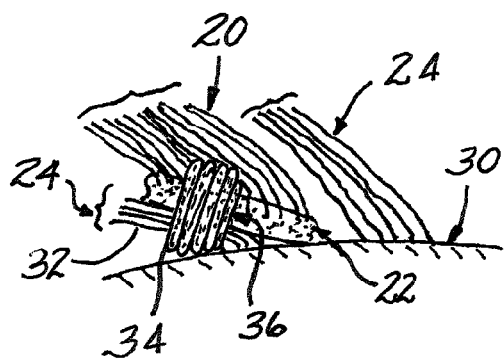
FIG. 3 is an enlarged diagrammatic fragmentary cross-sectional view illustrating the results of a currently-practiced method for attaching supplemental hair to existing natural hair at a site indicated by the arrow 3 in FIG. 1.
Figure 4:
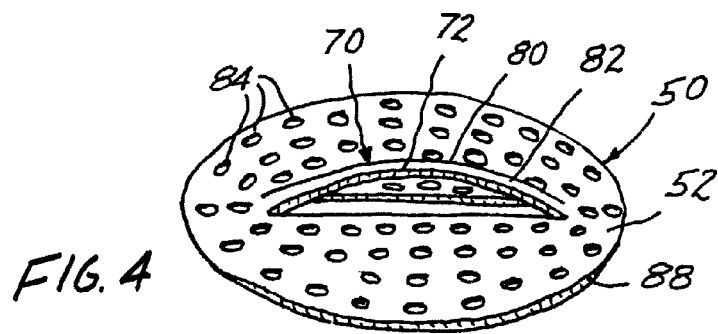
FIG. 4 is a pictorial view of a device constructed in accordance with the present invention.
Figure 5:
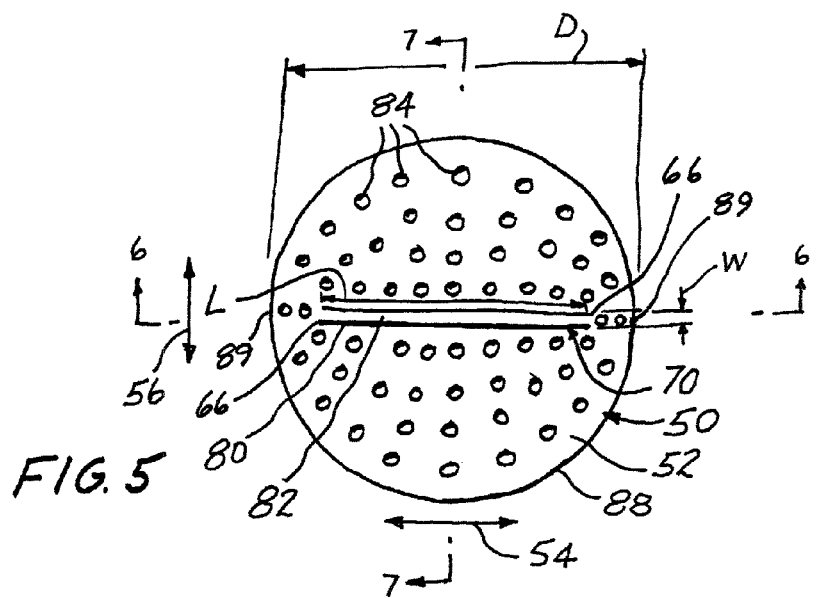
FIG. 5 is a top plan view, slightly smaller in scale, of the device of FIG. 4.
Figure 6:
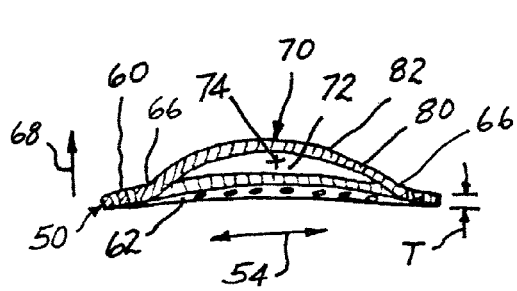
FIG. 6 is a longitudinal cross-sectional view taken along line 6-6 of FIG. 5.
Figure 7:
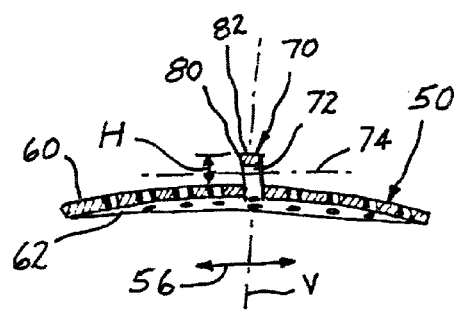
FIG. 7 is a lateral cross-sectional view taken along line 7-7 of FIG. 5.

Referring now to the drawing, and especially to FIGS. 1 through 3 thereof, in a currently-practiced procedure, supplemental hair 20, which is woven or otherwise affixed to a web-like basal member 22, is attached to existing natural hair 24 on a person's head 30 to supplement the natural hair 24 and provide an enhanced, fuller, more aesthetically pleasing appearance. Attachment is attained by securing the basal member 22 to tufts, such as tuft 32, of natural hair 24, as by threads 34 at locations 36 selected to deploy the supplemental hair 20 over the head 30 so as to meld the supplemental hair 20 with the existing natural hair 24 and emulate a natural disposition of hair, while the locations 36 themselves skillfully are hidden from view by surrounding natural hair 38 to complete the desired natural look. However, as time passes, the natural hair 24 in tuft 32 will grow out, carrying with it the attachment locations 36 and adversely affecting the desired natural appearance. IN addition, the locations 36 may become exposed to view, further compromising a natural look. Such eventual growth effectively will destroy the sought-after natural appearance and gives rise to a requirement for adjustments to be made from time to time to once again hide attachment locations 36 and regain the desired natural appearance.

Turning now to FIGS. 4 through 7, the present invention provides a fitting 50 constructed for placement at a selected location on a person's head, as will be demonstrated below, embedded just beneath the outer surface of the person's scalp, to provide a site for securement of supplemental hair, independent of any natural hair present on the person's head. To that end, fitting 50 includes a base 52 extending in longitudinal directions 54 and in lateral directions 56, and having an obverse surface 60 and a reverse surface 62. A bridge 70 is integral with the base 52 and extends in the longitudinal directions 54, the bridge 70 extending between longitudinally opposite ends 66 and rising in an latitudinal direction 68 from the obverse surface 60 of the base 54 to establish an eye 72 between the bridge 70 and the obverse surface 60, the eye 72 providing an open path 74 extending beneath the bridge 70 in the lateral directions 56.

Bridge 70 has a span 80 with a continuous, smooth-contoured upper surface 82, span 80 being arched, within a vertical plane V, for purposes to be described more fully below. In the preferred construction, span 80 is unitary with base 52, bridge 70 having been struck from base 52 to displace the bridge 70 from the base 52 and establish span 80 and smooth-contoured upper surface 82, in a relatively simple, unitary structure. A plurality of openings 84 extend through base 52, rendering base 52 foraminate, for purposes to be described below. In the illustrated preferred embodiment, fitting 50 is constructed of a biocompatible metal, such as titanium or stainless steel; however, synthetic polymeric materials are available for the purpose. Typically, base 52 is provided with a circular perimeter 88 having a predetermined diameter D of about ten millimeters, while bridge 70 provides span 80 with a prescribed length L just short of the predetermined diameter D, preferably about seventy percent of the diameter D, that is, a length L of about seven millimeters. In this manner, each of the opposite ends 66 of the bridge 70 is spaced from a corresponding adjacent portion 89 of the perimeter 88 of the base 52, thereby maintaining the structural integrity of fitting 50, while assuring that the fitting 50 is anchored securely upon embedding the fitting 50, as will be described below. In addition, the length L enables a gradual rise in span 80 to a height H of about two millimeters above the base 52, while a width W of about one-half a millimeter provides a very limited profile. The base 52 and span 80 preferably have a thickness T of about one-half a millimeter. Preferably, reverse surface 62 has a concave configuration, for purposes to be described below, while obverse surface 60 has a convex configuration.

With reference now to FIGS. 8 through 15, as well as to FIGS. 4 through 7, a person 90 has natural hair 92 growing about the person's head 94 and desires to supplement the natural hair 92 to establish an enhanced appearance provided by a fuller head of hair. In the practice of the method of the present invention, supplemental hair for that purpose is secured to the person's head 94 as follows: A plurality of fittings 50 are embedded beneath outer surface 100 of the person's scalp 110 to provide attachment sites 112 for the attachment of supplemental hair. The location of each attachment site 112 is selected in relation to existing natural hair 92 to assure melding of the supplemental hair with the natural hair 92 and to attain a natural appearance in which the attachment sites 112 will be hidden from view.

Figure 9:
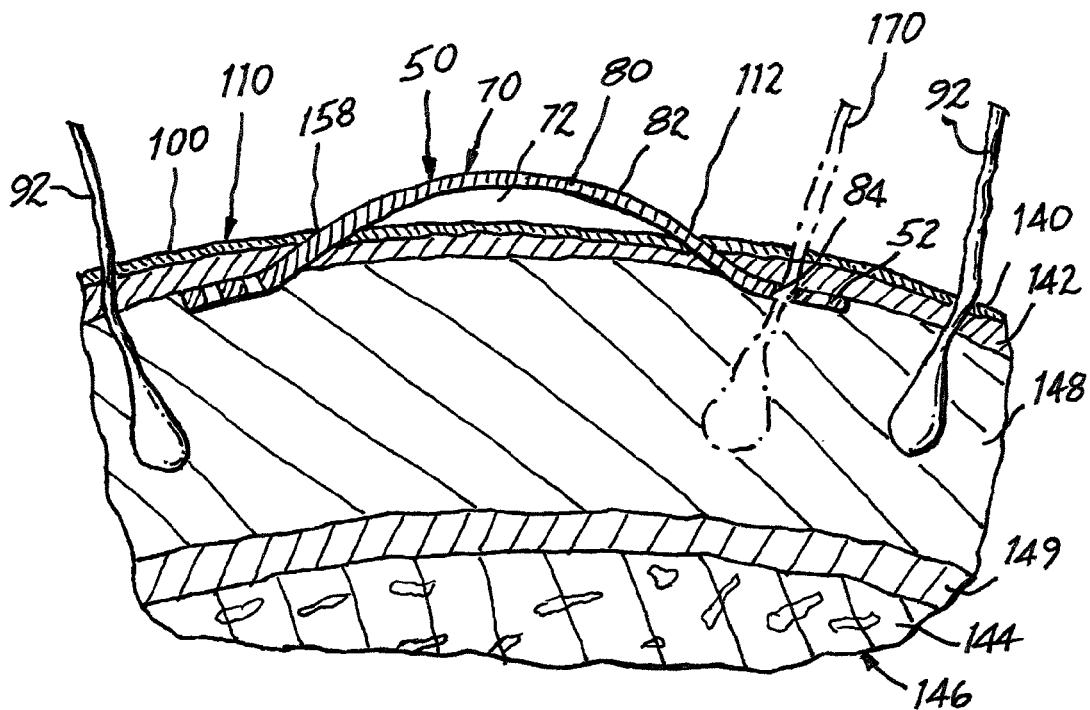
FIG. 9 is a much enlarged, somewhat diagrammatic fragmentary cross-sectional view taken along line 9-9 of FIG. 8.
Figure 10:
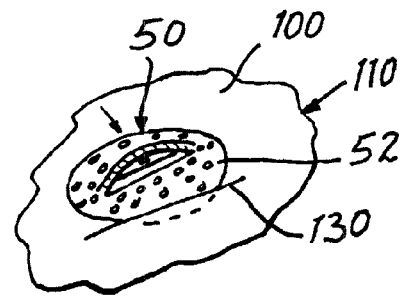
FIGS. 10 through 13 are pictorial views demonstrating a method practiced in accordance with the present invention.
Figure 11:
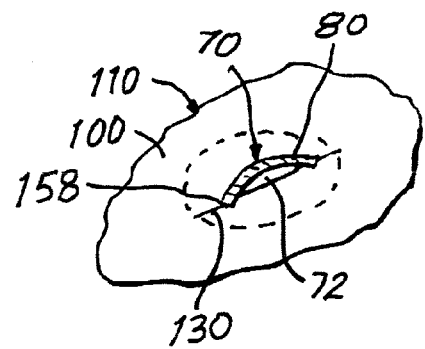

Each fitting 50 is embedded beneath the outer surface 100 of the scalp 110 by making a relatively short and shallow incision 130 in the scalp 110, incision 130 having a length approximately equal to the diameter D of the perimeter 88 of the base 52 of fitting 50, as seen in FIG. 10, and a depth which penetrates the epidermis 140 and extends through the derma 142 of scalp 110. Base 52 then is inserted and seated beneath the epidermis 140 and the derma 142, preferably juxtaposed with the derma 142, to secure the fitting 50 within the scalp 110, with the base 52 lying just below the outer surface 100 and spaced away from the bone 144 of the person's skull 146 by subcutaneous cellular tissue 148 and muscle tissue 149, as seen in FIG. 9, enabling securement of the fitting 50 with a minimally invasive procedure. Once the fitting 50 is seated, the incision 130 is closed over the base 52 and around the bridge 70, in longitudinal directions 54 and in lateral directions 56, so that the span 80 projects above the outer surface 100 of the scalp 110 and rises gradually from the scalp 110 to expose eye 72, as seen in FIG. 11.

Figure 12:
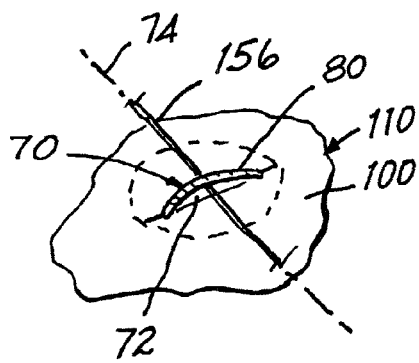
Figure 13:
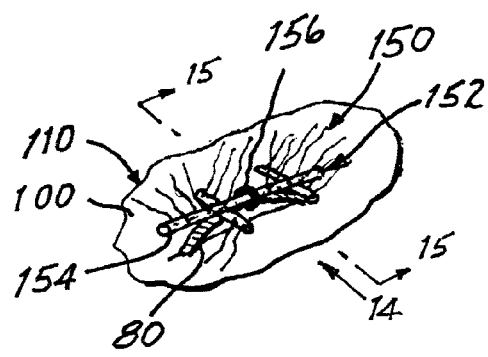
Figure 14:
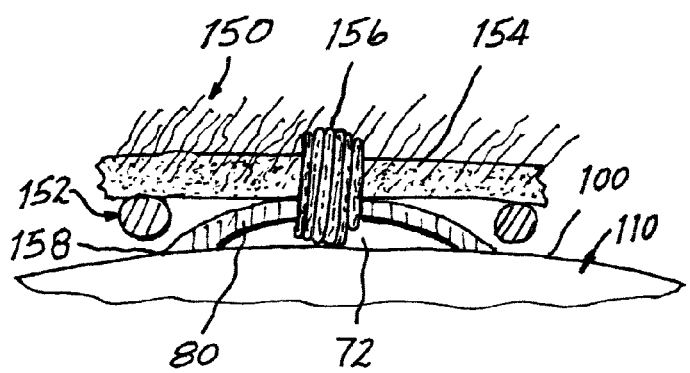
FIG. 14 is an enlarged, somewhat diagrammatic view taken in the direction of the arrow 14 in FIG. 13.
Figure 15:
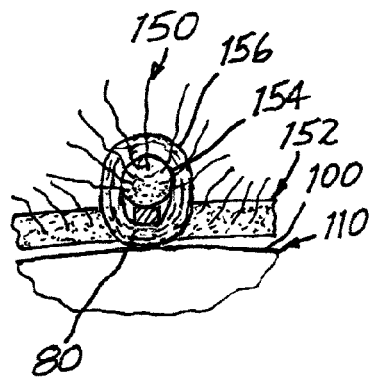
FIG. 15 is an enlarged, somewhat diagrammatic cross-sectional view taken along the one 15-15 of FIG. 13.

With an eye 72 exposed at each attachment site 112, supplemental hair 150 is attached to each fitting 50. Thus, as before, supplemental hair 150 is affixed to a web-like basal member 152 of strands 154 which are available for securement to a span 80 by a ligature in the form of a thread 156 passed through eye 72, along path 74 and beneath span 80, as seen in FIG. 12, and then around a strand 154, as seen in FIG. 13. Because securement of supplemental hair 150 now is accomplished independent of the existing natural hair 92, attachment sites 112 can be placed at locations skillfully selected, independent of the population and location of natural hair 92, to assure appropriate melding of supplemental hair 150 with natural hair 92 for an aesthetically pleasing enhanced natural look. In addition, should there be a dearth of available natural hair 92, fittings 50 can be located, independent of existing natural hair 92, to provide for the attachment of supplemental hair 150 for creating a full and natural-appearing head of hair.

Figure 8:
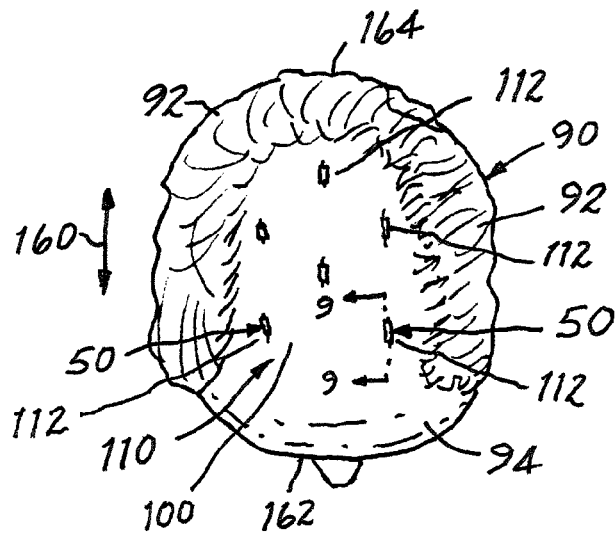
FIG. 8 is a top plan view of the head of a person showing devices of FIG. 4 installed in accordance with the method of the present invention.

The configuration of fitting 50 facilitates the embedding of fittings 50 wherever necessary throughout the head 94 of person 90. Thus, the concave configuration of the reverse surface 62 of base 52 substantially follows the contour of the head 94 and assures a firm seating of each fitting 50 at a selected attachment site 112. Further, the smooth-contoured upper surface 82 of span 80 of bridge 70, together with the longitudinal length L, the lateral width W and the continuous, arched configuration of span 80, not only establishes a substantially unobtrusive attachment site 112, to assist in hiding each fitting 50 from view, but provides a smooth transition at 158 between the outer surface 100 of scalp 110 and the upper surface 82 of span 80, offering little or no resistance to the conduct of regular hair maintenance, such as cleansing and grooming. The very limited projection of the span 80 above the outer surface 100 of scalp 110, together with the limited width W, renders the span 80 unobtrusive and enables cleansing and grooming without significant interference from fittings 50. The longitudinal direction of the span 80 of bridge 70, in combination with the arched configuration of span 80, allows each fitting 50 to be oriented in a preferred front-to-back orientation of the fittings 50, that is, aligned with directions 160 extending between the front 162 and the back 164 of the person's head 94, as seen in FIG. 8, so as to present essentially no impediment to combs and brushes ordinarily run across the head 94, and through the hair on the head 94, in directions aligned with directions 160 and the front-to-back orientation of the span 80 of the fitting 50.

With supplemental hair 150 secured to each fitting 50, rather than to existing hair 92, the attachment sites 112 will remain unaffected by growth over time of the natural hair 92. Thus, adjustments over time no longer are necessary in order to maintain the natural look sought by the addition of supplemental hair 150. It is noted that the foraminate construction of base 52 enables natural hair to grow through the base 52 where hair follicles are present for such growth, as illustrated in phantom at 170 in FIG. 9.

It will be seen then that the present invention attains all of the objects and advantages summarized above, namely: Provides a human head with one or more attachment sites for securing hair at strategic locations to supplement natural hair present on the head and attain an enhanced appearance independent of the population and location of natural hair present on the head; facilitates the attachment of supplemental hair to a human head at one or more locations selected for best attaining a natural aesthetic appearance; enables the establishment of strategically located hair attachment sites, utilizing simple, minimally invasive procedures; establishes an aesthetically pleasing appearance capable of long-term service without requiring periodic adjustments to maintain the pleasing appearance; permits the conduct of regular hair care without the necessity for extraordinary procedures to compensate for the presence of secured supplemental hair; simplifies the attainment of a secure and reliable attachment for supplemental hair to a person's head; encourages widespread adoption of the attachment of supplemental hair to enhance appearance; provides for a reliable attachment of supplemental hair for exemplary long-term performance.

It is to be understood that the above detailed description of preferred embodiments of the invention is provided by way of example only. Various details of design, construction and procedure may be modified without departing from the true spirit and scope of the invention as set forth in the appended claims.

The embodiments of the invention in which an exclusive property or privilege is claimed are defined as follows:

1. A fitting for placement at a selected location on a person's head, embedded beneath the outer surface of the person's scalp to secure the fitting at the selected location, to enable securement of hair to the person's head, the fitting comprising:

a base extending in longitudinal and lateral directions for placement between the outer surface of the scalp and the underlying bone of the person's skull, spaced from both the outer surface and the bone, the base having an obverse surface and a reverse surface; and a bridge integral with the base, the bridge extending in longitudinal directions between opposite ends and being raised from the base intermediate the opposite ends in an latitudinal direction to establish an eye between the bridge and the obverse surface of the base, the eye providing an open path extending in lateral directions, the bridge having a continuous, smooth contoured upper surface configuration extending from end to end of the opposite ends and spaced latitudinally from the obverse surface to pass over the eye, such that upon embedding the base beneath the outer surface of the scalp, the contoured configuration of the bridge will project latitudinally from the scalp unobtrusively, while exposing the eye for reception of a ligature which will secure hair to the fitting.

2. The fitting of claim 1 wherein the bridge has a prescribed longitudinal length and includes a span having an arched configuration along the prescribed longitudinal length, the arched configuration providing a smooth transition between the upper surface configuration of the bridge and the outer surface of scalp, upon embedding the base beneath the outer surface of the scalp.

3. The fitting of claim 2 wherein the base has a perimeter with a predetermined diameter along the longitudinal directions, and the prescribed longitudinal length of the bridge is less than the predetermined diameter such that each of the opposite ends is spaced from a corresponding portion of the perimeter of the base.

4. The fitting of claim 3 wherein the prescribed length of the bridge is about seventy percent of the predetermined diameter of the perimeter of the base.

5. The fitting of claim 2 wherein the span rises a shallow distance in the latitudinal direction above the obverse surface of the base.

6. The fitting of claim 2 wherein the base has a perimeter with a predetermined diameter of about ten millimeters along the longitudinal directions, the prescribed longitudinal length of the bridge is about seven millimeters, and the span rises about two millimeters in the latitudinal direction above the obverse surface of the base.

7. The fitting of claim 6 wherein the span has a width of about one-half a millimeter extending in the lateral directions.

8. The fitting of claim 7 wherein the bridge is unitary with the base.

9. The fitting of claim 1 wherein the reverse surface of the base has a concave configuration.

10. The fitting of claim 9 wherein the obverse surface of the base has a convex configuration.

11. The fitting of claim 1 wherein the base includes a foraminate configuration.

12. The fitting of claim 1 wherein the bridge is unitary with the base.

* * * * *